(12) United States Patent
Clemons et al.

(10) Patent No.: US 10,576,405 B2
(45) Date of Patent: Mar. 3, 2020

(54) SCENT-RELEASING AIR FILTER ASSEMBLY

(71) Applicants: Vertis Clemons, Conyers, GA (US);
Evette Clemons, Conyers, GA (US)

(72) Inventors: Vertis Clemons, Conyers, GA (US);
Evette Clemons, Conyers, GA (US)

(*) Notice: Subject to any disclaimer, the term of this patent is extended or adjusted under 35 U.S.C. 154(b) by 139 days.

(21) Appl. No.: 15/834,463

(22) Filed: Dec. 7, 2017

(65) Prior Publication Data

US 2018/0161715 A1 Jun. 14, 2018

Related U.S. Application Data

(60) Provisional application No. 62/431,772, filed on Dec. 8, 2016.

(51) Int. Cl.
| | |
|---|---|
| *B01D 46/00* | (2006.01) |
| *B01D 46/10* | (2006.01) |
| *B01D 39/16* | (2006.01) |
| *A61L 9/12* | (2006.01) |
| *B01D 46/52* | (2006.01) |
| *B01D 39/18* | (2006.01) |
| *A61L 9/04* | (2006.01) |

(52) U.S. Cl.
CPC .......... *B01D 46/0038* (2013.01); *A61L 9/042* (2013.01); *A61L 9/12* (2013.01); *B01D 39/1623* (2013.01); *B01D 39/18* (2013.01); *B01D 46/0012* (2013.01); *B01D 46/10* (2013.01); *B01D 46/521* (2013.01); *A61L 2209/14* (2013.01); *A61L 2209/16* (2013.01); *A61L 2209/22* (2013.01); *B01D 2239/04* (2013.01)

(58) Field of Classification Search
CPC ................ B01D 39/18; B01D 39/1623; B01D 46/0012; B01D 46/0038; B01D 46/10; B01D 46/521; B01D 2239/04; B01D 2239/045; A61L 9/042; A61L 9/12; A61L 2209/14; A61L 2209/16; A61L 2209/22
USPC ............... 96/222, 396; 55/490, 497; 239/34; 261/DIG. 88; 422/120
See application file for complete search history.

(56) References Cited

U.S. PATENT DOCUMENTS

| | | | | |
|---|---|---|---|---|
| 4,065,262 A | * | 12/1977 | Petroff ................... | B01D 46/12 239/289 |
| 4,563,333 A | * | 1/1986 | Frigon ................... | A62B 23/04 422/122 |
| 4,604,114 A | * | 8/1986 | Ward ..................... | B01D 46/10 239/60 |

(Continued)

*Primary Examiner* — Frank M Lawrence, Jr.

(57) ABSTRACT

A scent-releasing air filter assembly for freshening air includes a shell that defines an interior space. The shell is configured to couple in-line to an air circulation unit. A fibrous material is positioned in and substantially occupies the interior space. A reservoir, which is coupled to the shell and configured to contain a fluid, is in fluid communication with the interior space. The fibrous material is permeated by the fluid that flows from the reservoir. Each of a plurality of holes is positioned in a respective opposing side of the shell. The holes are configured to allow entry of air into the interior space from a first face of the shell and to permit exit of the air from a second face of the shell. The fibrous material is configured to remove solid particulates from the air concurrent with the release of a fragrance from the fluid to the air.

17 Claims, 4 Drawing Sheets

(56) References Cited

U.S. PATENT DOCUMENTS

| | | | |
|---|---|---|---|
| 4,959,087 A * | 9/1990 | Kappernaros | A61L 9/122 239/60 |
| 5,019,352 A | 5/1991 | Gonzalez | |
| 5,240,487 A | 8/1993 | Kung | |
| 5,240,653 A * | 8/1993 | Ramkissoon | A61L 9/12 239/56 |
| 5,258,051 A | 11/1993 | Anderson | |
| 5,858,045 A * | 1/1999 | Stemmer | B01D 46/0036 55/486 |
| D679,792 S | 4/2013 | Hollingsworth | |
| 2005/0103880 A1 | 5/2005 | Taite | |
| 2006/0272304 A1 * | 12/2006 | Schupp | A61L 9/04 55/501 |
| 2012/0234175 A1 | 9/2012 | Sanchez | |

\* cited by examiner

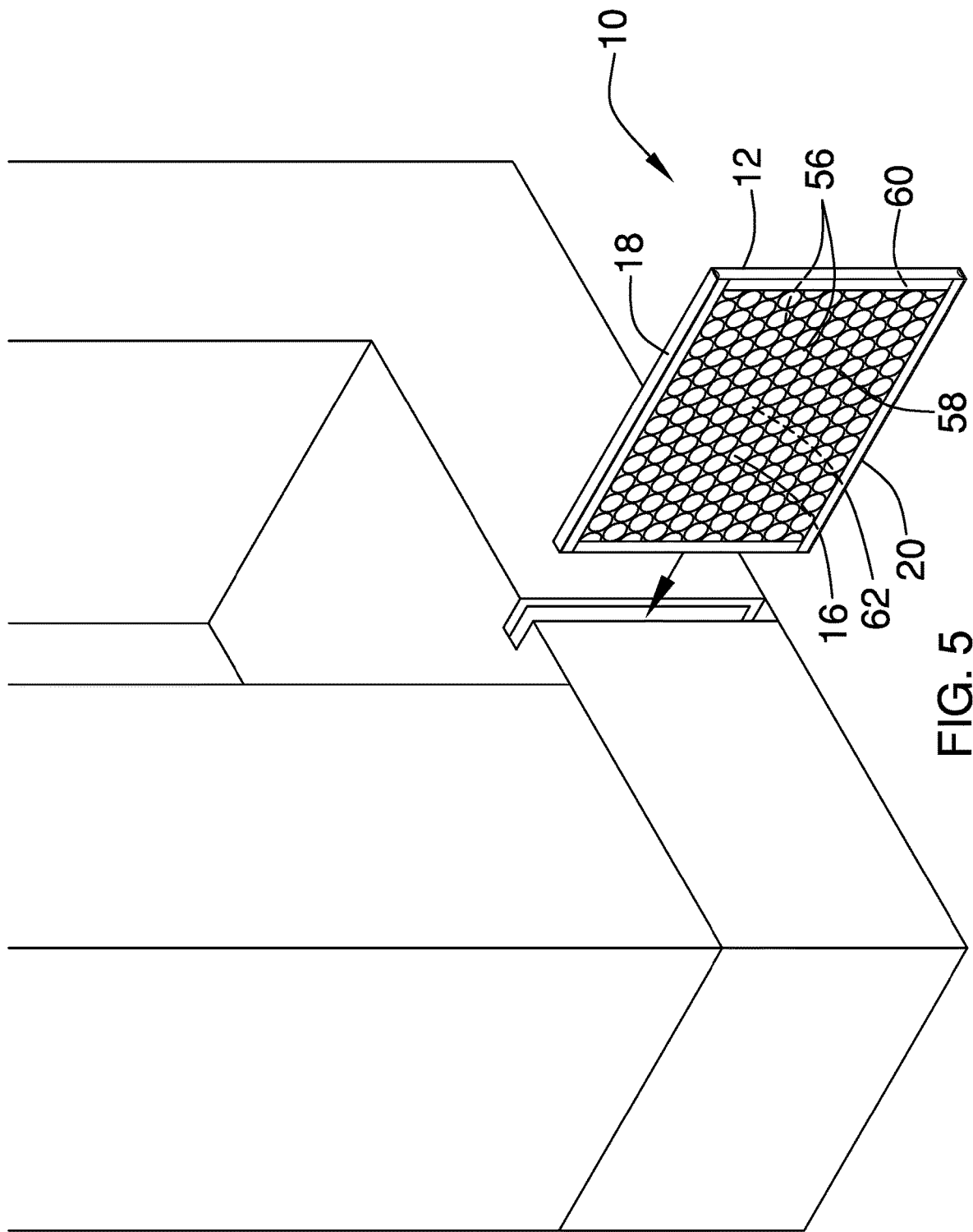

SCENT-RELEASING AIR FILTER ASSEMBLY

CROSS-REFERENCE TO RELATED APPLICATIONS

I hereby claim the benefit under 35 U.S.C. Section 119(e) of U.S. Provisional application 62/431,772 filed on Dec. 8, 2016.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to air filter assemblies and more particularly pertains to a new air filter assembly for freshening air.

BRIEF SUMMARY OF THE INVENTION

An embodiment of the disclosure meets the needs presented above by generally comprising a shell that defines an interior space. The shell is configured to couple in-line to an air circulation unit. A fibrous material is positioned in and substantially occupies the interior space. A reservoir, which is coupled to the shell and configured to contain a fluid, is in fluid communication with the interior space. The fibrous material is permeated by the fluid that flows from the reservoir. Each of a plurality of holes is positioned in a respective opposing side of the shell. The holes are configured to allow entry of air into the interior space from a first face of the shell and to permit exit of the air from a second face of the shell. The fibrous material is configured to remove solid particulates from the air concurrent with the release of a fragrance from the fluid to the air.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 5 is an in-use view of an embodiment of the disclosure.

DETAILED DESCRIPTION OF THE INVENTION

Figure 1:
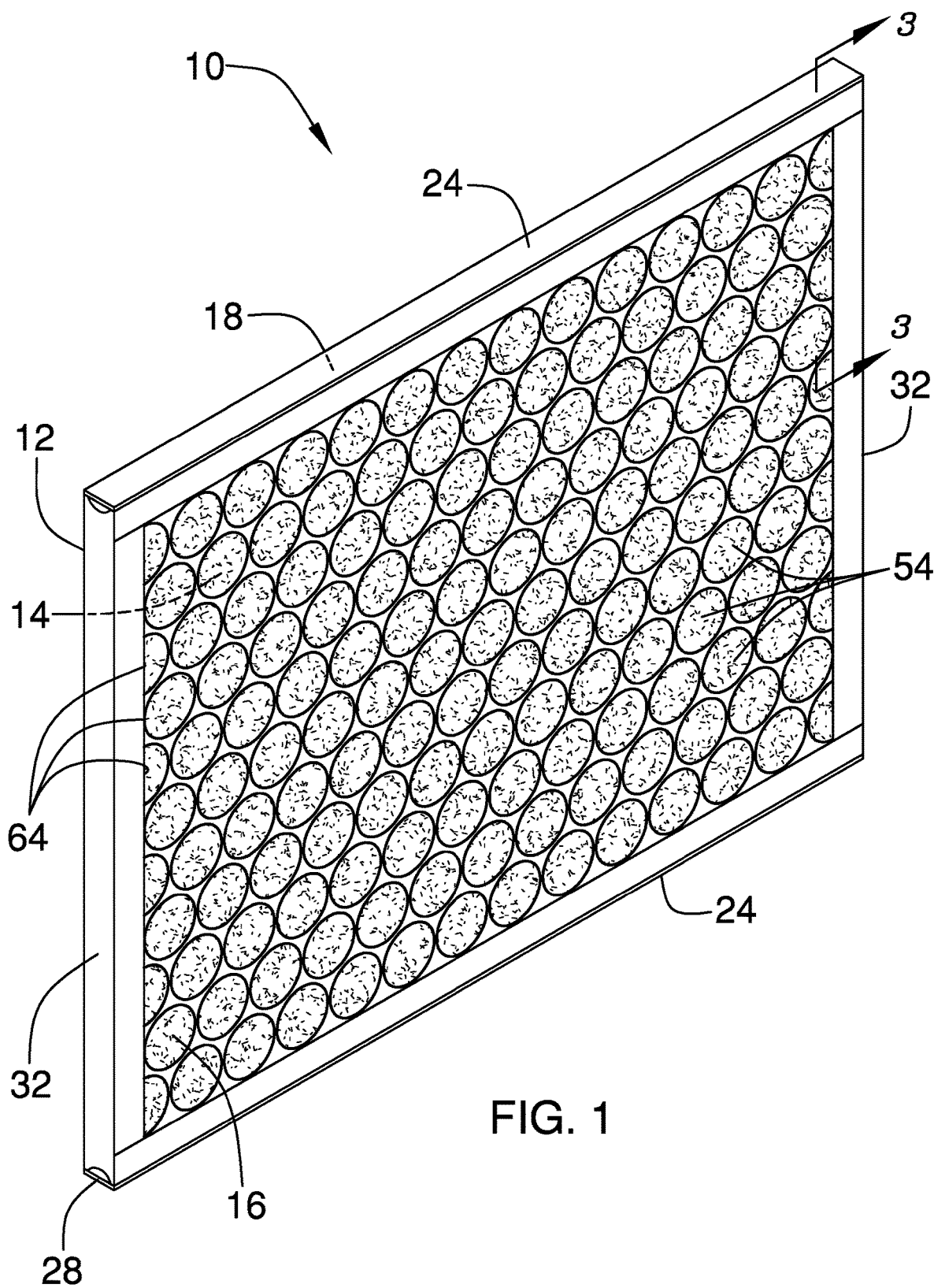
FIG. 1 is an isometric perspective view of a scent-releasing air filter assembly according to an embodiment of the disclosure.
Figure 2:
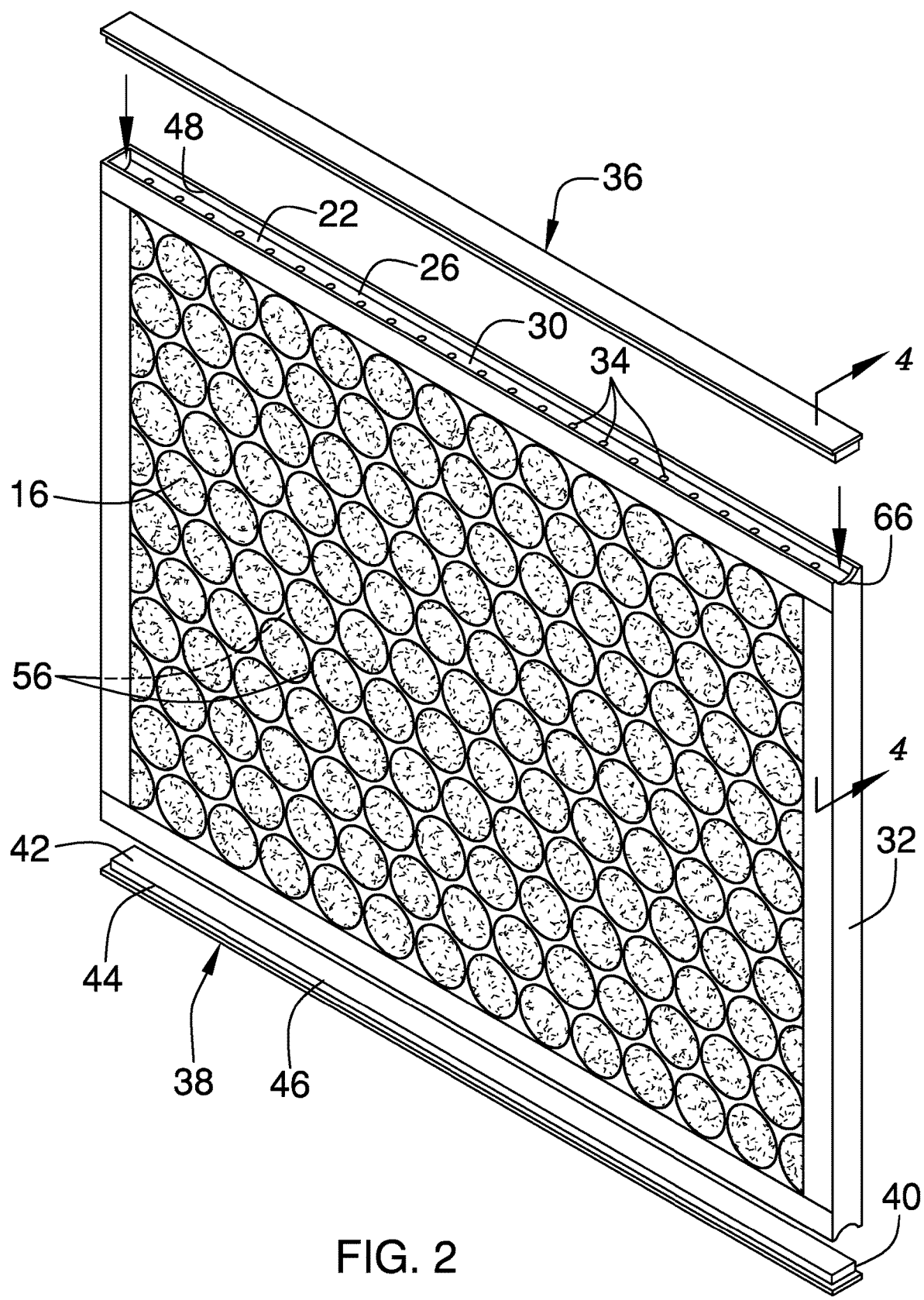
FIG. 2 is an exploded view of an embodiment of the disclosure.
Figure 4:
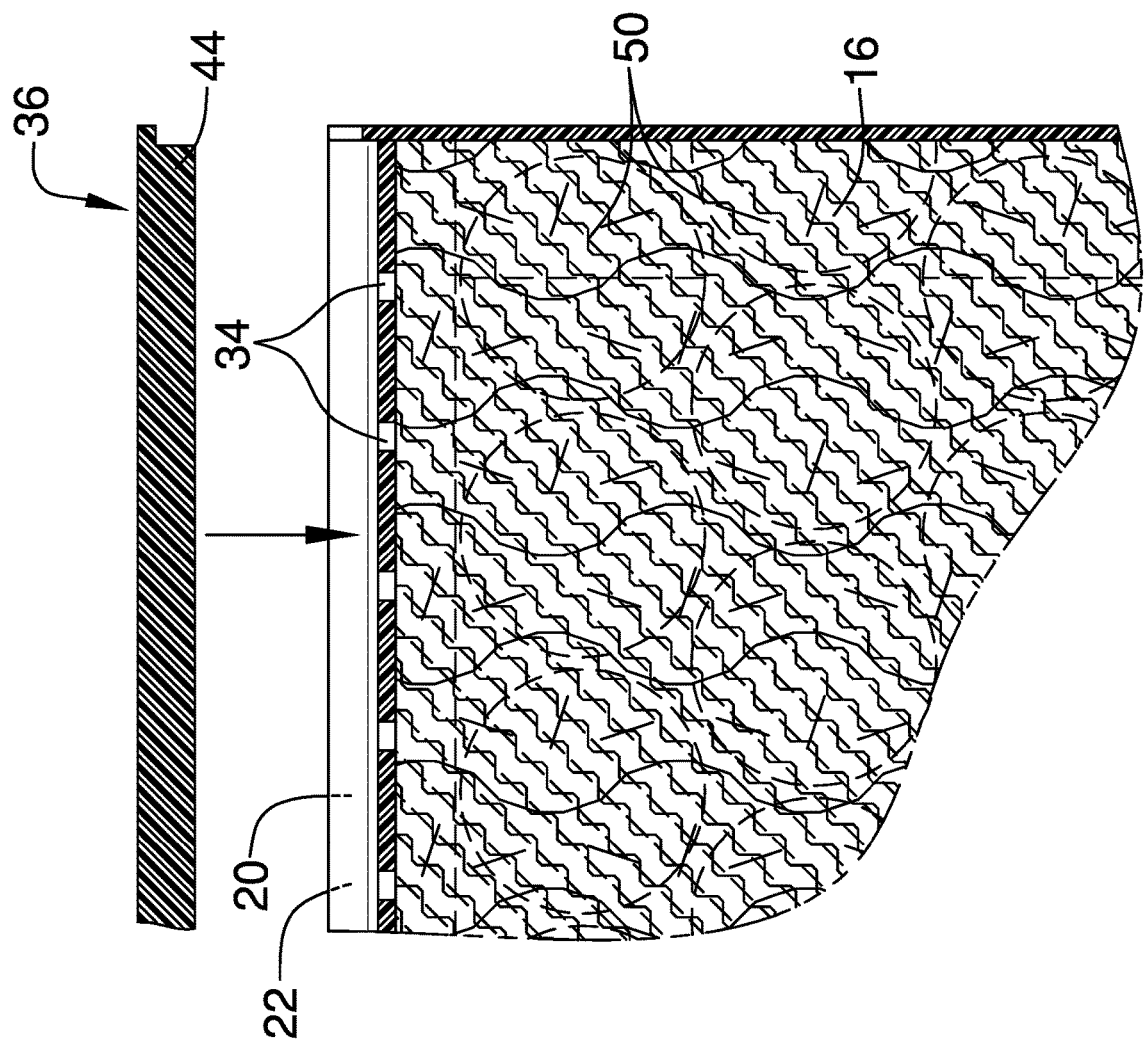
FIG. 4 is a cross-sectional view of an embodiment of the disclosure.
Figure 3:
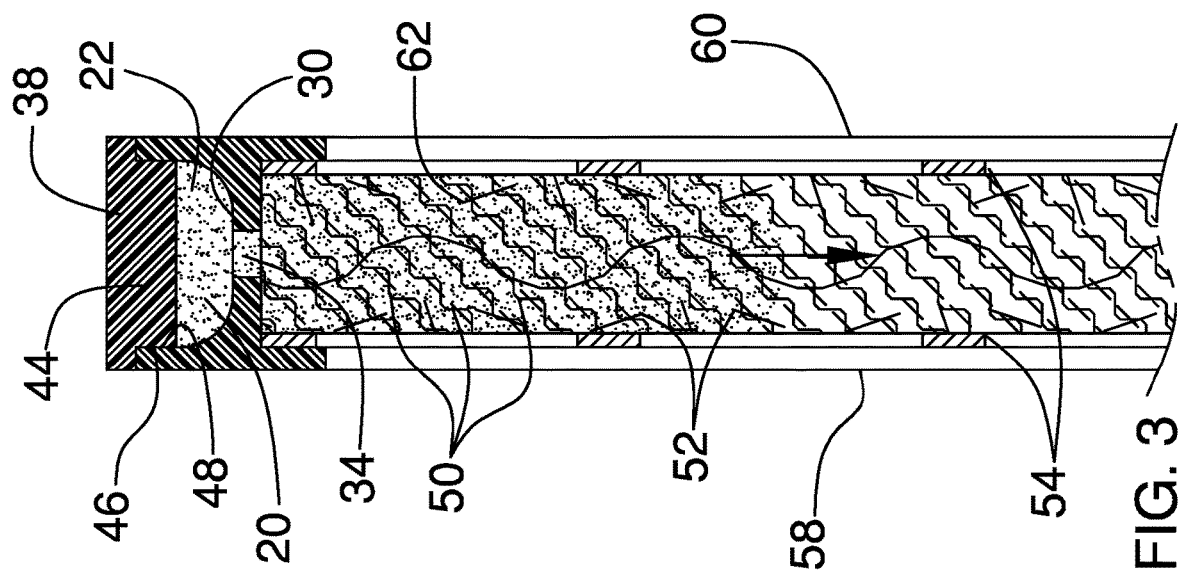
FIG. 3 is a cross-sectional view of an embodiment of the disclosure.

With reference now to the drawings, and in particular to FIGS. 1 through 5 thereof, a new air filter assembly embodying the principles and concepts of an embodiment of the disclosure and generally designated by the reference numeral 10 will be described.

As best illustrated in FIGS. 1 through 5, the scent-releasing air filter assembly 10 generally comprises a shell 12 that defines an interior space 14. The shell 12 is configured to couple in-line to an air circulation unit, such as a heating, ventilation, and air conditioning assembly. The shell 12 is rectangularly box shaped as needed for most air circulation units.

A fibrous material 16 is positioned in and substantially occupies the interior space 14. The fibrous material 16 comprises pleated paper, polyester, both pleated paper and polyester, or the like.

A reservoir 18 is coupled to the shell 12. The reservoir 18 is configured to contain a fluid 20. The reservoir 18 is in fluid communication with the interior space 14 whereby the fibrous material 16 is permeated by the fluid 20 that flows from the reservoir 18.

The reservoir 18 comprises a pair of troughs 22 that are positioned singly on opposing edges 24 of the shell 12. Each trough 22 is defined by an associated one of a pair of recesses 26 that extends into an associated opposing edge 24 of the shell 12. Each trough 22 has a bottom 30 that is concavely arcuate. Each recess 26 extends from proximate to opposing ends 32 of the shell 12.

Each of a plurality of orifices 34 is positioned in a respective bottom 30 of an associated trough 22 so that the associated trough 22 is in fluid communication with the interior space 14, whereby the fibrous material 16 is permeated by the fluid 20 that flows from the associated trough 22. The plurality of orifices 34 extends linearly between the opposing ends 32 of the shell 12.

Each of a pair of caps 36 is selectively couplable to a respective opposing edge 24 of the shell 12 to sealably close the associated trough 22. Each cap 36 comprises a slat 38 that is rabbeted around a circumference 40 of a lower face 42 of the slat 38 to define a protrusion 44. The protrusion 44 has an external perimeter 46 that is complementary to an inner perimeter 48 of the associated trough 22. The cap 36 is selectively couplable to the shell 12 by insertably engaging the protrusion 44 into the associated trough 22 to sealably close the associated trough 22.

A plurality of coils 50 is coupled to and is positioned in the fibrous material 16. Each coil 50 comprises a plurality of fibers 52. The coils 50 are positioned in the fibrous material 16 so that each coil 50 is positioned to channel the fluid 20 through the fibrous material 16, whereby the fibrous material 16 is permeated by the fluid 20 that flows from the reservoir 18.

Each of a plurality of cutouts 66 extends into a respective opposing end 32 of the shell 12 from the respective opposing edge 24 of the shell 12. Each cutout 66 is configured to selectively insert a digit of a hand of a user between a respective cap 36 and the shell 12 to decouple the respective cap 36 from the shell 12 to allow addition of the fluid 20 to the associated trough 22. The cutouts 66 are arcuate. The plurality of cutouts 66 comprises four cutouts 66 that are positioned singly adjacent to each corner 28 of the shell 12.

Each of a plurality of holes 54 is positioned in a respective opposing side 56 of the shell 12. The holes 54 are configured to allow entry of air into the interior space 14 from a first face 58 of the shell 12 and to permit exit of the air from a second face 60 of the shell 12. The fibrous material 16 is configured to remove solid particulates from the air concurrent with the release of a fragrance 62 from the fluid 20 to the air to freshen the air that is expelled from the air circulation unit. The plurality of holes 54 is positioned in a plurality of rows 64. Each row 64 extends linearly between the opposing ends 32 of the shell 12. The holes 54 are circularly shaped.

In use, each cutout 66 is configured to selectively insert the digit of the hand of the user between the respective cap 36 and the shell 12 to decouple the respective cap 36 from the shell 12 to allow addition of the fluid 20 to the associated trough 22. The cap 36 is selectively couplable to the shell 12 by insertably engaging the protrusion 44 into the associated trough 22 to sealably close the associated trough 22. The shell 12 the is coupled in-line to the air circulation unit just as a normal filter would be coupled. The orifices 34 are positioned in the respective bottom 30 so that the associated trough 22 is in fluid communication with the interior space 14. The coils 50 that are positioned in the fibrous material 16 channel the fluid 20 through the fibrous material 16, whereby the fibrous material 16 is permeated by the fluid 20 that flows from the associated trough 22. The holes 54 that are positioned in the shell 12 are configured to allow entry of the air into the interior space 14 from the first face 58 of the shell 12 and to permit exit of the air from the second face 60 of the shell 12. The fibrous material 16 is configured to remove the solid particulates from the air concurrent with the release of the fragrance 62 from the fluid 20 to the air to freshen the air that is expelled from the air circulation unit.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A scent-releasing air filter assembly comprising:
a shell defining an interior space, said shell being configured for coupling in-line to an air circulation unit;
a fibrous material positioned in and substantially occupying said interior space;
a reservoir coupled to said shell, said reservoir being in fluid communication with said interior space, said reservoir being configured for containing a fluid;
a plurality of holes, each said hole being positioned in a respective opposing side of said shell; and
wherein said reservoir is positioned on said shell such that said reservoir is in fluid communication with said interior space whereby said fibrous material is permeated by said fluid flowing from said reservoir, wherein said holes are positioned in said shell such that said holes are configured for entering of air into said interior space from a first face of said shell and for exiting of the air from a second face of said shell such that said fibrous material is configured for removing solid particulates from the air concurrent with said fluid releasing a fragrance to the air for freshening the air expelled from the air circulation unit; and
a plurality of coils coupled to and positioned in said fibrous material, each said coil comprising a plurality of fibers, wherein said coils are positioned in said fibrous material such that each said coil is positioned for channeling said fluid through said fibrous material whereby said fibrous material is permeated by said fluid flowing from said reservoir.

2. The assembly of claim 1, further including said shell being rectangularly box shaped.

3. The assembly of claim 1, further including said fibrous material comprising pleated paper.

4. The assembly of claim 1, further including said fibrous material comprising polyester.

5. The assembly of claim 3, further including said fibrous material comprising pleated paper and polyester.

6. The assembly of claim 1, further including said reservoir comprising:
a pair of troughs positioned singly on opposing edges of said shell, each said trough being defined by an associated one of a pair of recesses extending into an associated said opposing edge, each said trough having a bottom;
a plurality of orifices, each said orifice being positioned in a respective said bottom of an associated said trough such that said associated said trough is in fluid communication with said interior space; and
wherein said orifices are positioned in said respective said bottom such that said associated said trough is in fluid communication with said interior space whereby said fibrous material is permeated by said fluid flowing from said associated said trough.

7. The assembly of claim 6, further including said bottoms being concavely arcuate.

8. The assembly of claim 6, further including each said recess extending from proximate to opposing ends of said shell.

9. The assembly of claim 6, further including said plurality of orifices extending linearly between said opposing ends of said shell.

10. The assembly of claim 6, further including a pair of caps, each said cap being selectively couplable to a respective said opposing edge of said shell for sealably closing said associated said trough.

11. A scent-releasing air filter assembly comprising:
a shell defining an interior space, said shell being configured for coupling in-line to an air circulation unit;
a fibrous material positioned in and substantially occupying said interior space;
a reservoir coupled to said shell, said reservoir being in fluid communication with said interior space, said reservoir being configured for containing a fluid;
a plurality of holes, each said hole being positioned in a respective opposing side of said shell; and
wherein said reservoir is positioned on said shell such that said reservoir is in fluid communication with said interior space whereby said fibrous material is permeated by said fluid flowing from said reservoir, wherein said holes are positioned in said shell such that said holes are configured for entering of air into said interior space from a first face of said shell and for exiting of the air from a second face of said shell such that said fibrous material is configured for removing solid particulates from the air concurrent with said fluid releasing a fragrance to the air for freshening the air expelled from the air circulation unit;
said reservoir comprising
  a pair of troughs positioned singly on opposing edges of said shell, each said trough being defined by an associated one of a pair of recesses extending into an associated said opposing edge, each said trough having a bottom,
  a plurality of orifices, each said orifice being positioned in a respective said bottom of an associated said trough such that said associated said trough is in fluid communication with said interior space, and
  wherein said orifices are positioned in said respective said bottom such that said associated said trough is in fluid communication with said interior space whereby said fibrous material is permeated by said fluid flowing from said associated said trough;
a pair of caps, each said cap being selectively couplable to a respective said opposing edge of said shell for sealably closing said associated said trough; and
each said cap comprising a slat, said slat being rabbeted around a circumference of a lower face of said slat defining a protrusion, said protrusion having an external perimeter complementary to an inner perimeter of said associated said trough such that said cap is selectively couplable to said shell by insertably engaging said protrusion into said associated said trough for sealably closing said associated said trough.

12. The assembly of claim 11, further including a plurality of cutouts, each said cutout extending into a respective opposing end of said shell from said respective said opposing edge of said shell, wherein said cutouts are positioned in said shell such that each said cutout is configured for selectively inserting a digit of a hand of a user between a respective said cap and said shell for decoupling said respective said cap from said shell for adding said fluid to said associated said trough.

13. The assembly of claim 12, further including said cutouts being arcuate.

14. The assembly of claim 12, further including said plurality of cutouts comprising four said cutouts positioned singly adjacent to each corner of said shell.

15. The assembly of claim 1, further including said plurality of holes being positioned in a plurality of rows, each said row extending linearly between said opposing ends of said shell.

16. The assembly of claim 1, further including said holes being circularly shaped.

17. A scent-releasing air filter assembly comprising:
a shell defining an interior space, said shell being configured for coupling in-line to an air circulation unit, said shell being rectangularly box shaped;
a fibrous material positioned in and substantially occupying said interior space;
a reservoir coupled to said shell, said reservoir being in fluid communication with said interior space, said reservoir being configured for containing a fluid, wherein said reservoir is positioned on said shell such that said reservoir is in fluid communication with said interior space whereby said fibrous material is permeated by said fluid flowing from said reservoir, said reservoir comprising a pair of troughs positioned singly on opposing edges of said shell, each said trough being defined by an associated one of a pair of recesses extending into an associated said opposing edge, each said trough having a bottom, said bottoms being concavely arcuate, each said recess extending from proximate to opposing ends of said shell;
a plurality of orifices, each said orifice being positioned in a respective said bottom of an associated said trough such that said associated said trough is in fluid communication with said interior space, wherein said orifices are positioned in said respective said bottom such that said associated said trough is in fluid communication with said interior space whereby said fibrous material is permeated by said fluid flowing from said associated said trough, said plurality of orifices extending linearly between said opposing ends of said shell;
a pair of caps, each said cap being selectively couplable to a respective said opposing edge of said shell for sealably closing said associated said trough, each said cap comprising a slat, said slat being rabbeted around a circumference of a lower face of said slat defining a protrusion, said protrusion having an external perimeter complementary to an inner perimeter of said associated said trough such that said cap is selectively couplable to said shell by insertably engaging said protrusion into said associated said trough for sealably closing said associated said trough;
a plurality of coils coupled to and positioned in said fibrous material, each said coil comprising a plurality of fibers, wherein said coils are positioned in said fibrous material such that each said coil is positioned for channeling said fluid through said fibrous material whereby said fibrous material is permeated by said fluid flowing from said reservoir;
a plurality of cutouts, each said cutout extending into a respective said opposing end of said shell from said respective said opposing edge of said shell, wherein said cutouts are positioned in said shell such that each said cutout is configured for selectively inserting a digit of a hand of a user between a respective said cap and said shell for decoupling said respective said cap from said shell for adding said fluid to said associated said trough, said cutouts being arcuate, said plurality of cutouts comprising four said cutouts positioned singly adjacent to each corner of said shell;

a plurality of holes, each said hole being positioned in a respective opposing side of said shell, wherein said holes are positioned in said shell such that said holes are configured for entering of air into said interior space from a first face of said shell and for exiting of the air from a second face of said shell such that said fibrous material is configured for removing solid particulates from the air concurrent with said fluid releasing a fragrance to the air for freshening the air expelled from the air circulation unit, said plurality of holes being positioned in a plurality of rows, each said row extending linearly between said opposing ends of said shell, said holes being circularly shaped; and wherein said cutouts are positioned in said shell such that each said cutout is configured for selectively inserting the digit of the hand of the user between said respective said cap and said shell for decoupling said respective said cap from said shell for adding said fluid to said associated said trough, such that said cap is selectively couplable to said shell by insertably engaging said protrusion into said associated said trough for sealably closing said associated said trough, wherein said orifices are positioned in said respective said bottom such that said associated said trough is in fluid communication with said interior space, wherein said coils are positioned in said fibrous material such that each said coil is positioned for channeling said fluid through said fibrous material whereby said fibrous material is permeated by said fluid flowing from said associated said trough, wherein said holes are positioned in said shell such that said holes are configured for entering of the air into said interior space from said first face of said shell and for exiting of the air from said second face of said shell such that said fibrous material is configured for removing the solid particulates from the air concurrent with said fluid releasing the fragrance to the air for freshening the air expelled from the air circulation unit.

\* \* \* \* \*